United States Patent
Ono et al.

(10) Patent No.: US 9,695,462 B2
(45) Date of Patent: Jul. 4, 2017

(54) METHOD FOR EVALUATION OF DRUG EFFICACY OF A MEDICINE HAVING A THERAPEUTIC OR PREVENTIVE EFFECT AGAINST A DISEASE RELATED TO EL ACTIVITY AND A METHOD FOR SCREENING AN INHIBITOR OF EL ACTIVITY

(71) Applicant: SHIONOGI & CO., LTD., Osaka-shi, Osaka (JP)

(72) Inventors: Takashi Ono, Toyonaka (JP); Atsuko Yamamoto, Toyonaka (JP); Shuhei Shigaki, Toyonaka (JP)

(73) Assignee: SHIONOGI & CO., LTD., Osaka-shi (JP)

(*) Notice: Subject to any disclaimer, the term of this patent is extended or adjusted under 35 U.S.C. 154(b) by 83 days.

(21) Appl. No.: 14/437,941

(22) PCT Filed: Nov. 5, 2013

(86) PCT No.: PCT/JP2013/079814
§ 371 (c)(1),
(2) Date: Apr. 23, 2015

(87) PCT Pub. No.: WO2014/069651
PCT Pub. Date: May 8, 2014

(65) Prior Publication Data
US 2015/0291998 A1    Oct. 15, 2015

(30) Foreign Application Priority Data
Nov. 5, 2012   (JP) .................................. 2012-243324

(51) Int. Cl.
*C12Q 1/44*    (2006.01)
*G01N 33/92*   (2006.01)

(52) U.S. Cl.
CPC ............. *C12Q 1/44* (2013.01); *G01N 33/92* (2013.01); *G01N 2333/92* (2013.01);
(Continued)

(58) Field of Classification Search
None
See application file for complete search history.

(56) References Cited

U.S. PATENT DOCUMENTS

2003/0181353 A1* 9/2003 Nyce ................... A61K 45/06
514/1

FOREIGN PATENT DOCUMENTS

| JP | 2005-80608 A | 3/2005 |
|----|--------------|--------|
| JP | 2012-517219 A | 8/2012 |

(Continued)

OTHER PUBLICATIONS

Sliusar "Changes in phosphatidylinositol levels in the blood and its components in patients with leukemia" Gematologiia I transfuziologiia, vol. 35 Issue 10, 19-21, 1990, Abstract provided.*
(Continued)

*Primary Examiner* — Louise W Humphrey
*Assistant Examiner* — Charles Zoltan Constantine
(74) *Attorney, Agent, or Firm* — Birch, Stewart, Kolasch & Birch, LLP

(57) ABSTRACT

The present invention is related to a method for evaluation of drug efficacy of a medicine having a therapeutic or preventive effect against a disease related to EL activity wherein phosphatidylinositol or lysophosphatidylinositol is used as an indicator. The present invention is also related to a method for screening an inhibitor of EL activity using phosphatidylinositol and a kit for use in the method.

2 Claims, 6 Drawing Sheets

(52) U.S. Cl.
CPC ..... *G01N 2405/06* (2013.01); *G01N 2500/00* (2013.01); *G01N 2500/04* (2013.01); *G01N 2500/20* (2013.01); *G01N 2560/00* (2013.01)

(56) References Cited

FOREIGN PATENT DOCUMENTS

| WO | WO 00/57837 A2 | 10/2000 |
| WO | WO 2004/094393 A1 | 11/2004 |
| WO | WO 2010/092068 A1 | 8/2010 |

OTHER PUBLICATIONS

Broedl et al. "Endothelial Lipase: A Modulator of Lipoprotein Metabolism Upregulated by Inflammation", TCM, 2004, 14(5), 202-206.
Darrow et al. "A novel fluorogenic substrate for the measurement of endothelial lipase activity", J. Lipid Res., 2011, vol. 52, 374-382.
International Search Report, issued in PCT/JP2013/079814, dated Jan. 21, 2014.
Ishida et al. "ELISA System for Human Endothelial Lipase", Clin. Chem., Oct. 15, 2012, vol. 58, No. 12, p. 1656-1664.
Ishida et al. "Endothelial lipase is a major determinant of HDL level", The Journal of Clinical Investigation, 2003, 111(3), 347-355.
Ishida et al. "Endothelial Lipase Modulates Susceptibility to Atherosclerosis in Apolipoprotein-E-deficient Mice", The Journal of Biological Chemistry, 2004, 279(43), 45085-45092.
Jaye et al. "A novel endothelial-derived lipase that modulates HDL metabolism", Nature Genetics, 1999, 21,(4), 424-428.
Miksztowicz et al. "Endothelial Lipase Activity Predicts High-Density Lipoprotein Catabolism in Hemodialysis: Novel Phospholipase Assay in Postheparin Human Plasma", Arterioscler. Thromb. Vasc. Biol., Oct. 25, 2012, vol. 32, 3033-3040.
Written Opinion of the International Searching Authority, issued in PCT/JP2013/079814, dated Jan. 21, 2014.
English translation of International Preliminary Report on Patentability and Written Opinion mailed May 14, 2015, in PCT International Application No. PCT/JP2013/079814.
Extended European Search Report issued Mar. 31, 2016, in European Patent Application No. 13851614.1.
Muccioli, G, G., "Endocannabinoid biosynthesis and inactivation, from simple to complex," Drug Discovery Today (Jun. 2010), vol. 15, Nos. 11/12, pp. 474-483.
Yasuda et al., "Update on the Role of Endothelial Lipase in High-Density Lipoprotein Metabolism, Reverse Cholesterol Transport, and Atherosclerosis," Circulation Journal (2010), vol. 74, pp. 2263-2270.

* cited by examiner

METHOD FOR EVALUATION OF DRUG EFFICACY OF A MEDICINE HAVING A THERAPEUTIC OR PREVENTIVE EFFECT AGAINST A DISEASE RELATED TO EL ACTIVITY AND A METHOD FOR SCREENING AN INHIBITOR OF EL ACTIVITY

A method for evaluation of drug efficacy of a medicine having a therapeutic or preventive effect against a disease related to EL activity and a method for screening an inhibitor of EL activity.

TECHNICAL FIELD

The present invention relates to a method for measurement of the activity of vascular endothelial lipase (hereinafter, referred to EL), wherein phosphatidylinositol or lysophosphatidylinositol is used as an indicator. More specifically, the present invention relates to a method for evaluation of drug efficacy of a medicine having a therapeutic or preventive effect against a disease related to EL activity and a method for screening an inhibitor of EL activity.

BACKGROUND ART

EL is phospholipase belonging to triglyceride lipase (hereinafter, referred to TGL) family (Non-patent document 1). Human EL consists of 500 amino acid residues (NCBI Accession No. NP_006024.1) and mouse EL also consists of 500 amino acid residues. Lipoprotein lipase (hereinafter, referred to LPL) and hepatic lipase (hereinafter, referred to HL) are included in TGL family.

The analysis of EL knockout mice and EL transgenic mice revealed the involvement of EL in HDL cholesterol (hereinafter, referred to HDL-c) metabolism due to its strong phospholipase activity for HDL, and EL is noted as a determinant of HDL levels (Non-Patent Document 2). The negative correlation between coronary artery disease (hereinafter, referred to CAD) and plasma HDL-c levels has been known for a long time. HDL-c has been believed to show anti-atherogenic effect via anti-oxidant, anti-inflammatory and reverse cholesterol transport action and low HDL-c cholesteremia has been recognized as one of the risk factors for CAD. Therefore, EL inhibitor can be a therapeutic agent against CAD, and the increase in HDL-c levels and the decrease of atherosclerotic lesion area have actually been reported in the animal model of disease using EL-knockout mice (Non-Patent Document 3).

These findings exhibit utility of a specific inhibitor for EL as a therapeutic agent against lipid metabolism disorder and atherosclerosis.

In evaluation of drug efficacy of EL inhibitor, it is important to grasp the degree of inhibition of EL in blood by administered drug in order to understand the potency of drug efficacy. However, because other enzymes having lipase activity similar to EL exist in blood, the finding of assay method which can detect EL activity specifically is a problem to be solved for selecting a promising inhibitor.

The lipase having higher activity than EL exists in blood under the general assay condition well known (Non-Patent Document 4). Thereby, as EL activity can not be measured accurately, it is difficult to accurately determine inhibition rate of administered EL inhibitor in blood. When blood is collected to measure EL activity in non-clinical study, it is necessary to administer a large amount of heparin intravenously in order to release and collect EL from blood vessel wall, but intravenous injection of a large amount of heparin to a subject is not allowed in clinical trial. Therefore, the marker as an indicator of EL activity is essential for clinical trial, whereas there has never been any report about the presence of maker for EL activity.

Non-Patent Document 1: Nature Genetics., 1999, vol. 21 (4), p. 424-428

Non-Patent Document 2: TCM., 2004, vol. 14 (5), p. 202-206

Non-Patent Document 3: The Journal of Biological Chemistry., 2004, vol. 279 (43), p. 45085-45092

Non-Patent Document 4: The Journal of Clinical Investigation, 2003, vol. 111 (3), p. 347-355

SUMMARY OF THE INVENTION

Problem to be Solved by the Invention

An objective of the present invention relates to measure EL activity specifically in sample collected from non-clinical and clinical specimens. In principle, it is impossible to administer a large amount of heparin intravenously in clinical trial. Therefore, an objective of the present invention is to measure EL activity specifically without administering a large amount of heparin to a subject.

The present inventors have contemplated that the exploring substrate specific for EL from phospholipids in plasma lipoprotein might be the best strategy for solving the problem of the improvement in accuracy and selectivity of assay for EL activity and the identification of marker of EL activity. The present inventors found that phosphatidylinositol can be used as a specific substrate for EL by intensive studies, and achieved the present invention.

To be more specific, the present invention provides below [1] to [10]:

[1] A method for measurement of EL activity, wherein phosphatidylinositol or lysophosphatidylinositol is used as an indicator.

[2] A method for evaluation of drug efficacy of a medicine having a therapeutic or preventive effect against a disease related to EL activity, comprising (1) a step for comparing a concentration of phosphatidylinositol or lysophosphatidylinositol in a sample obtained from a mammal after the administration of a test substance with a concentration of phosphatidylinositol or lysophosphatidylinositol in a sample obtained from the mammal before the administration of the test substance, and (2) a step for evaluating the test substance as a medicine having a therapeutic or preventive effect against a disease related to EL activity when the concentration of phosphatidylinositol or lysophosphatidylinositol in the sample obtained from the mammal after the administration of the test substance is increased relative to the concentration of phosphatidylinositol or lysophosphatidylinositol in the sample obtained from the mammal before the administration of the test substance.

[3] A method for evaluation of drug efficacy of a medicine having a therapeutic or preventive effect against a disease related to EL activity, comprising (1) a step for comparing a concentration of phosphatidylinositol in a sample obtained from a mammal after the administration of a test substance with a concentration of phosphatidylinositol in a sample obtained from the mammal before the administration of the test substance, and (2) a step for evaluating the test substance as a medicine having a therapeutic or preventive effect against a disease related to EL activity when the concentration of phosphatidylinositol in the sample obtained from the mammal after the administration of the test substance is increased relative to the concentration of phosphatidylinositol in the sample obtained from the mammal before the administration of the test substance.

[4] A method for evaluation of drug efficacy of a medicine having a therapeutic or preventive effect against a disease related to EL activity, comprising
(1) a step for comparing a concentration of lysophosphatidylinositol in a sample obtained from a mammal after the administration of a test substance with a concentration of lysophosphatidylinositol in a sample obtained from the mammal before the administration of the test substance, and
(2) a step for evaluating the test substance as a medicine having a therapeutic or preventive effect against a disease related to EL activity when the concentration of lysophosphatidylinositol in the sample obtained from the mammal after the administration of the test substance is increased relative to the concentration of lysophosphatidylinositol in the sample obtained from the mammal before the administration of the test substance.

[5] The method described in [2]-[4], wherein the sample is blood, serum or plasma.

[6] A method for screening an inhibitor of EL activity, comprising
(1) a step for contacting phosphatidylinositol, a test substance and EL,
(2) a step for comparing a concentration of phosphatidylinositol when the test substance is contacted with a concentration of phosphatidylinositol when the test substance is not contacted and
(3) a step for selecting the test substance as an inhibitor of EL activity when the concentration of phosphatidylinositol when the test substance is contacted is increased relative to the concentration of phosphatidylinositol when the test substance is not contacted.

[7] The method described in [6], wherein phosphatidylinositol is phosphatidylinositol-liposomes, phosphatidylinositol-HDL, phosphatidylinositol-reconstituted HDL or phosphatidylinositol-detergent mixed micelles.

[8] A method for screening an inhibitor of EL activity, comprising
(1) a step for contacting phosphatidylinositol, a test substance and EL,
(2) a step for comparing a concentration of lysophosphatidylinositol when the test substance is contacted with a concentration of lysophosphatidylinositol when the test substance is not contacted, and
(3) a step for selecting the test substance as an inhibitor of EL activity when the concentration of lysophosphatidylinositol when the test substance is contacted is decreased relative to the concentration of lysophosphatidylinositol when the test substance is not contacted.

[9] The method described in [8], wherein phosphatidylinositol is phosphatidylinositol-liposomes, phosphatidylinositol-HDL, phosphatidylinositol-reconstituted HDL or phosphatidylinositol-detergent mixed micelles.

[10] A kit for use in the method according to [6]-[9]

Effect of the Invention

A method for evaluation of drug efficacy of a medicine having a therapeutic or preventive effect against a disease related to EL activity, wherein a concentration of phosphatidylinositol or lysophosphatidylinositol is used as an indicator, is provided by the present invention. A method for screening an inhibitor of EL activity using phosphatidylinositol and a kit for use in the method is also provided by the present invention.

MODE FOR CARRYING OUT THE INVENTION

Figure 1:
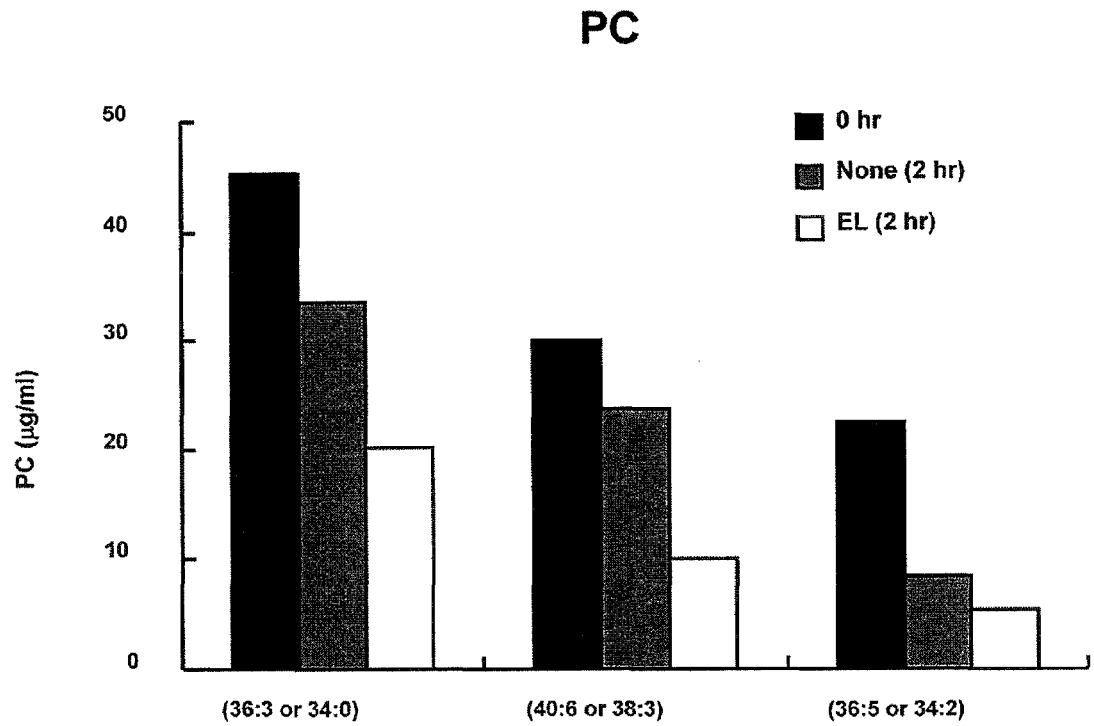
FIG. 1 shows the change in phosphatidylcholine (hereinafter, also called PC) levels, when mouse preheparin plasma is incubated with or without EL. The horizontal axis and the vertical axis indicate molecular species of phosphatidylcholine and phosphatidylcholine levels, respectively.

A term in the present invention, unless specifically referred to, is used as the meaning commonly used in the art.

In one embodiment, the present invention provides a method for measurement of EL activity, wherein phosphatidylinositol or lysophosphatidylinositol is used as an indicator. The method includes a method for evaluation of drug efficacy of a medicine having a therapeutic or preventive effect against a disease related to EL activity, wherein phosphatidylinositol or lysophosphatidylinositol is used as an indicator, and a method for screening an inhibitor of EL activity, wherein phosphatidylinositol or lysophosphatidylinositol is used as an indicator.

Phosphatidylinositol is one of the acidic phospholipids with inositol in polar head group and is sometimes abbreviated as PI. Many kinds of molecular species consisting of the differences in combination of fatty acids at the sn-1 and sn-2 positions exist. For example, from molecular weight of phosphatidylinositol estimated from the results of analysis by mass spectrometry, if the predicted sum of the carbon number of fatty acid esterified at the sn-1 and sn-2 positions are 38 and the predicted sum of the double bond are 4, respectively, it is shown as 38:4.

Phosphatidylcholine is also called lecithin and sometimes abbreviated as PC. Many kinds of molecular species consisting of the differences in combination of fatty acids at the sn-1 and sn-2 positions exist. For example, from molecular weight of phosphatidylcholine estimated from the results of analysis by mass spectrometry, if the predicted sum of the carbon number of fatty acid esterified at the sn-1 and sn-2 positions are 36 and the predicted sum of the double bond are 3, respectively, it is shown as 36:3.

Phosphatidylethanolamine is sometimes abbreviated as PE. Many kinds of molecular species consisting of the differences in combination of fatty acids at the sn-1 and sn-2 positions exist. For example, from molecular weight of phosphatidylethanolamine estimated from the results of analysis by mass spectrometry, if the predicted sum of the carbon number of fatty acid esterified at the sn-1 and sn-2 positions are 40 and the predicted sum of the double bond are 6, respectively, it is shown as 40:6.

EL means vascular endothelial lipase which is a kind of phospholipase belonging to TGL family. The GenBank Accession numbers of human, rabbit and mouse EL are Accession No. NP_006024.1, NP_001182567.1 and NP_034850.3, respectively. In the present specification, EL includes not only the proteins consisting of amino acid sequence registered in said GenBank Accession numbers but also the proteins having the same amino acid sequences as those described above except that one amino acid or some amino acids is deleted, substituted or added. However, these are limited to proteins having phospholipase activity equal to EL registered in said GenBank Accession numbers.

A disease related to EL activity means dyslipidemia, hyperlipidemia, arteriosclerosis, atherosclerosis, hypercholesterolemia, hypertriglyceridemia, diabetes, obesity, syndrome X and the like.

In another embodiment, the present invention provides a method for evaluation of drug efficacy of a medicine having a therapeutic or preventive effect against a disease related to EL activity, comprising (1) a step for comparing a concentration of phosphatidylinositol or lysophosphatidylinositol in a sample obtained from an mammal after the administration of a test substance with a concentration of phosphatidylinositol or lysophosphatidylinositol in a sample obtained from the mammal before the administration of the test substance, and (2) a step for evaluating the test substance as a medicine having a therapeutic or preventive effect against a disease related to EL activity when the concentration of phosphatidylinositol or lysophosphatidylinositol in the sample obtained from the mammal after the administration of the test substance is altered relative to the concentration of phosphatidylinositol or lysophosphatidylinositol in the sample obtained from the mammal before the administration of the test substance.

A disease related to EL activity means dyslipidemia, hyperlipidemia, arteriosclerosis, atherosclerosis, hypercholesterolemia, hypertriglyceridemia, diabetes, obesity, syndrome X and the like.

In the step (1) of the above method, the test substances include any known and novel compounds, and examples thereof include nucleic acids, carbohydrates, lipids, proteins, peptides, organic low molecular compounds, compound library prepared using the technology of combinatorial chemistry, random peptide library prepared by solid phase synthesis or phage display method or natural products derived from microorganisms, animals and plants, and marine organism.

In the step (1) of the above method, for example, the quantification of phosphatidylinositol levels in the sample can be performed by mass spectrometry, for example, with reference to Analytical Letters, 2006, vol. 39, p. 957-972. On the other hand, the quantification of lysophosphatidylinositol levels in the sample can be performed by TLC development with reference to unexamined patent application 2010-63470 or mass spectrometry with reference to Chromatographia., 2010, vol. 72 (7/8), p. 659-664.

In the step (1) of the above method, any species of mammal is permissible. And if a sample is obtained from a mammal, any sample is permissible, but blood, serum or plasma is preferred.

In the step (2) of the above method, a concentration of phosphatidylinositol or lysophosphatidylinositol in a sample obtained from a mammal after the administration of a test substance is compared with a concentration of phosphatidylinositol or lysophosphatidylinositol in a sample obtained from the mammal before the administration of the test substance. The comparison of a concentration of phosphatidylinositol or lysophosphatidylinositol is preferably carried out on the basis of the presence or absence of a significant difference. A concentration of phosphatidylinositol or lysophosphatidylinositol in the sample obtained from the mammal before the administration of the test substance may be acceptable both a concentration of phosphatidylinositol or lysophosphatidylinositol measured in advance and at the same time against measurement after the administration of the test substance, but a concentration of phosphatidylinositol or lysophosphatidylinositol measured at the same time is preferable in terms of accuracy of the experiment or reproducibility of the experiment.

In the step (1) and (2) of the above method, it is never necessary to release EL into blood. Therefore, the present invention has the advantage that the present evaluation method do not need the intravenous injection of heparin in collecting blood from a subject and is also applicable for a subject in clinical trial.

In another embodiment, the present invention provides a method for screening an inhibitor of EL activity, comprising
(1) a step for contacting phosphatidylinositol, a test substance and EL,
(2) a step for comparing a concentration of phosphatidylinositol when the test substance is contacted with a concentration of phosphatidylinositol when the test substance is not contacted, and
(3) a step for selecting the test substance as an inhibitor of EL activity when the concentration of phosphatidylinositol when the test substance is contacted is increased relative to the concentration of phosphatidylinositol when the test substance is not contacted.

Phosphatidylinositol used in the step (1) of the above method is acceptable for any forms as long as phosphatidylinositol is contained, even if phosphatidylinositol is phosphatidylinositol-liposomes, phosphatidylinositol-HDL, phosphatidylinositol-reconstituted HDL or phosphatidylinositol-detergent mixed micelles.

Phosphatidylinositol-liposomes mean dispersion in solution of phosphatidylinositol or the mixture of phosphatidylinositol and lipid, prepared by the mechanical process like the sonication. The lipids used in the said mixture include, for example, lipids contained in blood. Phosphatidylinositol-liposomes can be prepared appropriately with reference to The journal of Lipids Research, 1976, vol. 17 (3), p. 239-247.

Phosphatidylinositol-HDL means phosphatidylinositol-induced artificial HDL prepared by mixing phosphatidylinositol with HDL. The HDL in the said phosphatidylinositol-induced artificial HDL includes, for example, HDL or its components, namely, HDL2 and HDL3.

Phosphatidylinositol-reconstituted HDL means the reconstituted HDL prepared by mixing phosphatidylinositol or the mixture of phosphatidylinositol and lipids with apoproteins. The lipids in the said mixture include, for example, lipids contained in blood. The apoproteins used for the preparation of phosphatidylinositol-reconstituted HDL include, for example, apoproteins contained in blood. Phosphatidylinositol-reconstituted HDL can be prepared appropriately with reference to The Journal of Biological Chemistry, 1982, vol. 257 (8), p. 4535-4540.

Phosphatidylinositol-detergent mixed micelles mean the mixed micelles prepared by solubilizing phosphatidylinositol or the mixture of phosphatidylinositol and lipid by detergent. The lipids in the said mixture include, for example, lipids contained in blood. The detergents used for the preparation of phosphatidylinositol-detergent mixed micelles include, for example, ionic and non-ionic detergents. Phosphatidylinositol-detergent mixed micelles can be prepared appropriately with reference to The Journal Biological Chemistry, 1988, vol. 263 (12), p. 5724-5731.

The test substances which are subjected to the screening methods include any known and novel compounds, and examples thereof include nucleic acids, carbohydrates, lipids, proteins, peptides, organic low molecular compounds, the compound library prepared using the technology of combinatorial chemistry, random peptide library prepared by solid phase synthesis and phage display method and the natural products derived from microorganisms, animals and plants, and marine organism.

In the step (2) of the above method, for example, the quantification of phosphatidylinositol levels in the sample can be performed by mass spectrometry, for example, with reference to Analytical Letters, 2006, vol. 39, p. 957-972 or can be performed by measuring NEFA levels produced from phosphatidylinositol of substrate.

In the step (3) of the above method, a concentration of phosphatidylinositol when the test substance is contacted is compared with a concentration of phosphatidylinositol when the test substance is not contacted. The comparison of a concentration of phosphatidylinositol is preferably carried out on the basis of the presence or absence of a significant difference. A concentration of phosphatidylinositol when the test substance is not contacted may be acceptable both a concentration of phosphatidylinositol measured in advance and at the same time against measurement of a concentration of phosphatidylinositol when the test substance is contacted, but a concentration of phosphatidylinositol measured at the same time is preferable in terms of accuracy of the experiment or reproducibility.

An inhibitor of EL activity discovered by the screening has a therapeutic or preventive effect against a disease related to EL activity, namely has a therapeutic or preventive effect against dyslipidemia, hyperlipidemia, arteriosclerosis, atherosclerosis, hypercholesterolemia, hypertriglyceridemia, diabetes, obesity, syndrome X and the like.

In another embodiment, the present invention provides a method for screening an inhibitor of EL activity, comprising
(1) a step for contacting phosphatidylinositol, a test substance and EL,
(2) a step for comparing a concentration of lysophosphatidylinositol when the test substance is contacted with a concentration of lysophosphatidylinositol when the test substance is not contacted, and
(3) a step for selecting the test substance as an inhibitor of EL activity when the concentration of lysophosphatidylinositol when the test substance is contacted is decreased relative to the concentration of lysophosphatidylinositol when the test substance is not contacted.

In the step (2) of the above method, the concentration of lysophosphatidylinositol which is a lipolytic product of phosphatidylinositol is measured. The quantification of lysophosphatidylinositol levels in the sample can be performed by TLC development with reference to unexamined patent application 2010-63470 or mass spectrometry with reference to Chromatographia., 2010, vol. 72 (7/8), p. 659-664.

The present invention is described below in more detail by the way of examples. However, the present invention is not limited to the following examples.

Example 1

Figure 2:
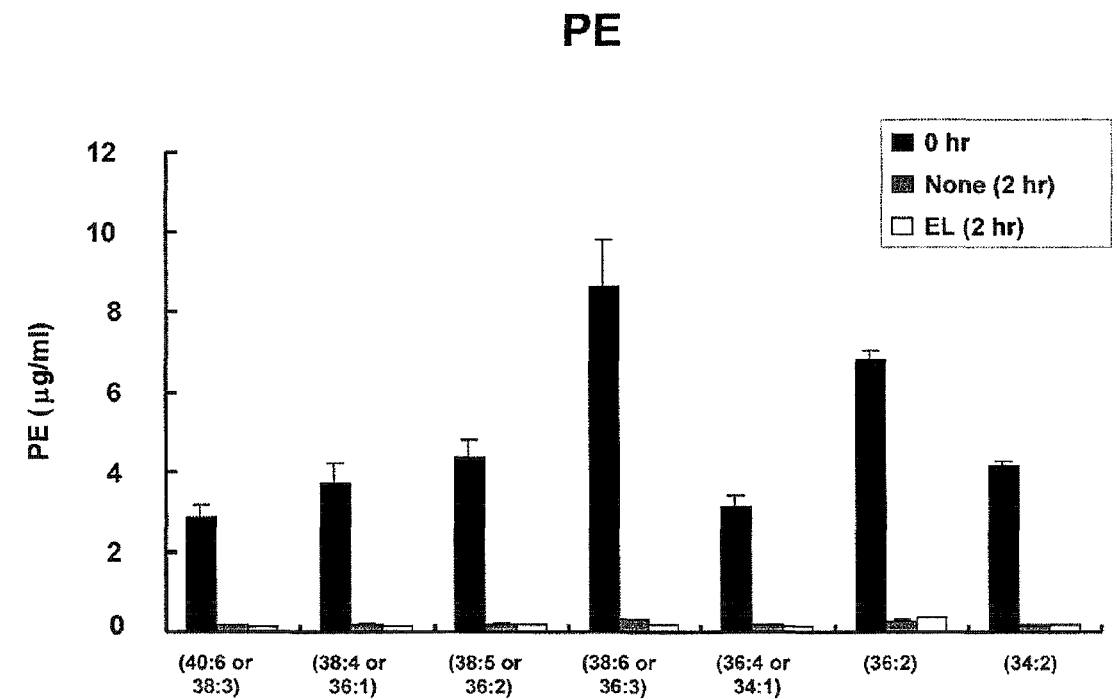
FIG. 2 shows the change in phosphatidylethanolamine (hereinafter, also called PE) levels, when mouse preheparin plasma is incubated with or without EL. The horizontal axis and the vertical axis indicate molecular species of phosphatidylethanolamine and phosphatidylethanolamine levels, respectively.
Figure 3:
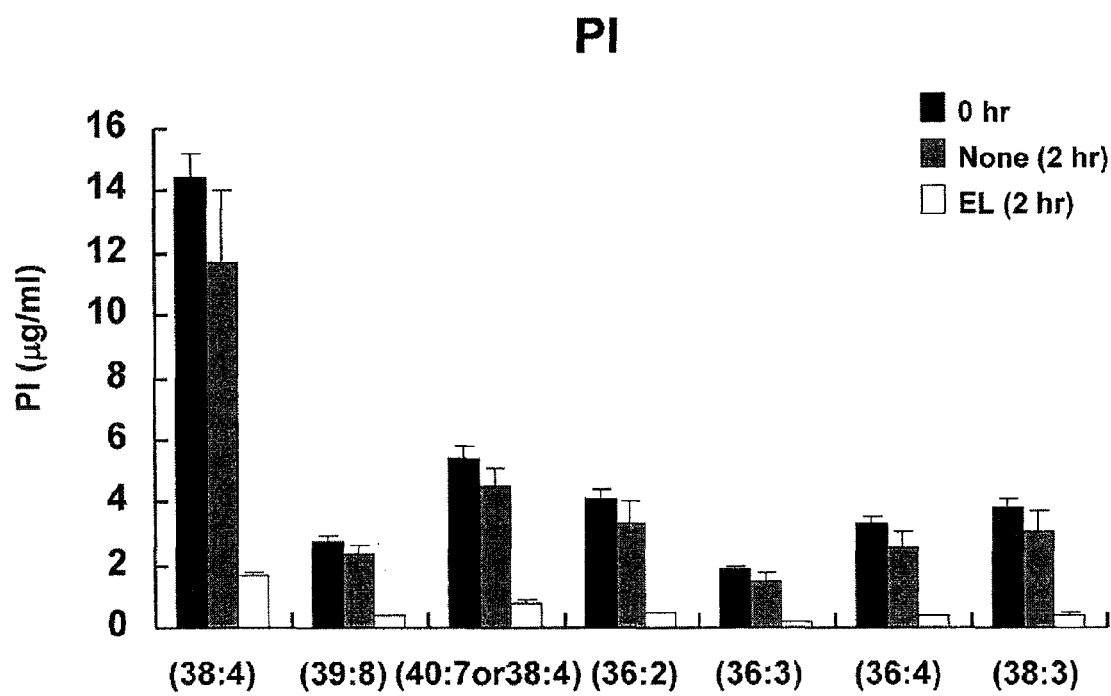
FIG. 3 shows the change in phosphatidylinositol (hereinafter, also called PI) levels, when mouse preheparin plasma is incubated with or without EL. The horizontal axis and the vertical axis indicate molecular species of phosphatidylinositol and phosphatidylinositol levels, respectively.

Verification of Substrate Specificity of EL for Phospholipids in Mouse Plasma Lipoproteins
The pcDNA-DEST40 (Invitrogen Corp.) cloned DNA encoding mouse EL was transfected into Freestyle 293F cells and the cells were cultured at 37° C. for 2 days in an atmosphere of 8% $CO_2$. The cells were collected by centrifugation of the culture medium, suspended in Freestyle 293 Expression Medium (Invitrogen Corp.) containing 20 U/ml heparin and incubated at 37° C. for 45 min. After that, the supernatant obtained by removing the cells by centrifugation was used as mouse EL enzyme solution. The reaction mixture consisting of preheparin plasma of C57BL/6J mice and mouse EL enzyme solution (9:1, v/v) was incubated at 37° C. for 2 hr and added EDTA (final concentration of 10 mM) to terminate the reaction. After that, various phospholipids in reaction solution were quantified by mass spectrometry with reference to Analytical Letters 2006., vol. 39, p. 957-972. From the comparison of the change in each phospholipid levels between incubation without and with EL addition, the phospholipids showing specific change for EL addition were explored (FIG. 1-3). As a result, the actions of lipase other than EL for phosphatidylcholine and phosphatidylethanolamine were found, whereas it became clear that EL alone showed the activity for phosphatidylinositol.

Example 2

Figure 4:
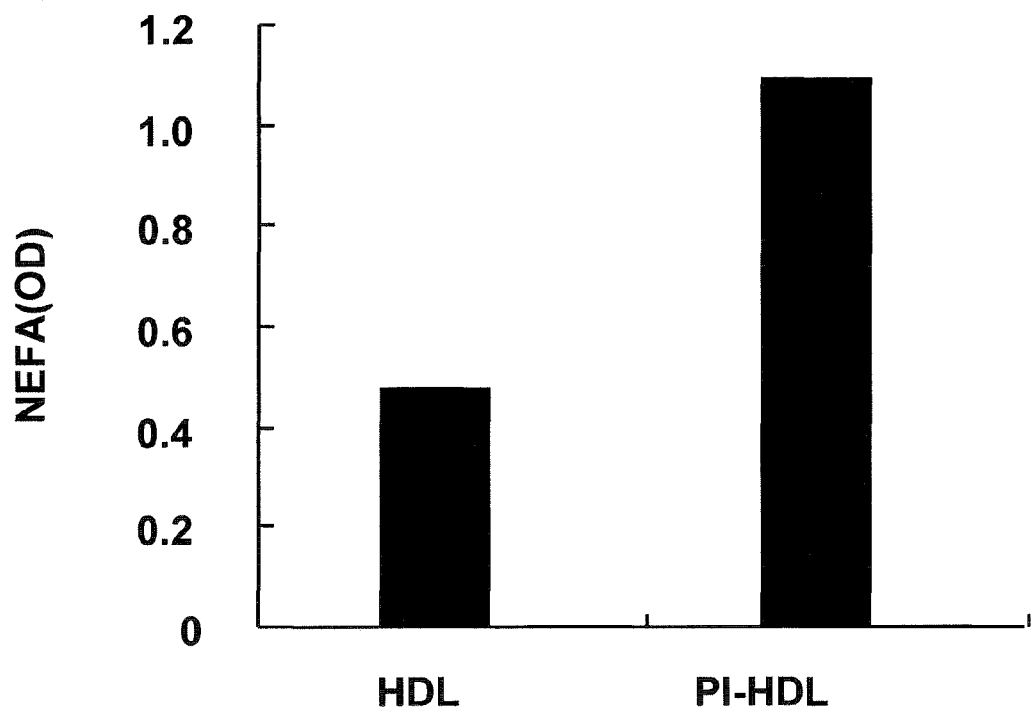
FIG. 4 shows mouse EL activity when phosphatidylinositol-induced HDL (hereinafter, also called PI-HDL) or HDL is used as a substrate. The horizontal axis and the vertical axis indicate the substrate used and the amount of non-esterified free fatty acid (hereinafter, also called NEFA), respectively.
Figure 5:
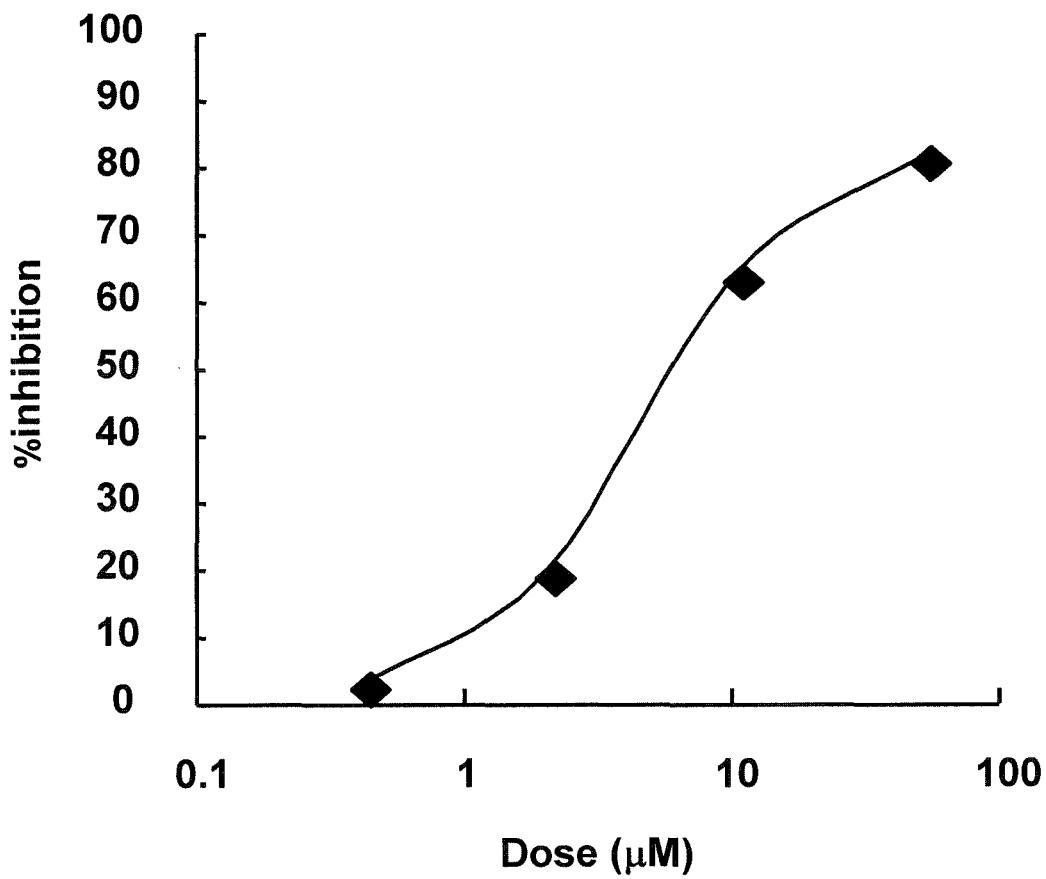
FIG. 5 shows the inhibitory effect of orlistat, which is known inhibitor of lipase, on mouse EL when PI-HDL is used as a substrate. The horizontal axis and the vertical axis indicate the concentration of orlistat and the inhibition rate, respectively.

Measurement of Mouse EL Activity and Evaluation of an Inhibitor of EL Activity Using Phosphatidylinositol-HDL as a Substrate Phosphatidylinositol (Avanti Polar Lipids Inc.) in chloroform was collected the necessary amount, which was completely evaporated the solvent to dryness under nitrogen. After addition of PBS, phosphatidylinositol-HDL induced phosphatidylinositol (2.5 mg/ml) into HDL (5 mg/ml) was prepared by mixing phosphatidylinositol vesicle prepared by sonication on ice with human HDL (Athens Research & Technology, Inc.) and incubating at 4° C. for 24 hr. The pcDNA-DEST40 (Invitrogen Corp.) cloned DNA encoding mouse EL was transfected into Freestyle 293F cells and the cells were cultured at 37° C. for 2 days in an atmosphere of 8% $CO_2$. The cells were collected by centrifugation of the culture medium, suspended in Freestyle 293 Expression Medium (Invitrogen Corp.) containing 20 U/ml heparin and incubated at 37° C. for 45 min. After that, the supernatant obtained by removing the cells by centrifugation was used as mouse EL enzyme solution. Phosphatidylinositol-HDL or HDL was added to reaction solution including 20 mM Tris-HCl buffer (pH 7.5), 0.5% bovine serum albumin, 4 mM calcium chloride and 150 mM sodium chloride to achieve a final concentration of 2 mg/ml and finally, mouse EL enzyme solution was added (total volume of 10 µl). After reaction at 37° C. for 2 hr, the amount of NEFA produced from substrate by EL was measured with NEFA C-test Wako (Wako Pure Chemical Industries, Ltd.) and the amount of NEFA (absorbance) was assumed an index of enzyme activity. The enzyme activity was calculated by subtracting the background value equivalent to the amount of endogenous NEFA without mouse EL enzyme solution from the value measured in enzyme reaction of EL (FIG. 4). As a result, mouse EL exhibited about 2-fold higher activity when using phosphatidylinositol-HDL as a substrate than when using HDL as a substrate, suggesting that phosphatidylinositol-HDL was higher sensitivity substrate for EL than HDL. Furthermore, when the inhibitory activity of a well-known lipase inhibitor, orlistat against mouse EL was examined using phosphatidylinositol-HDL as a substrate, a dose-dependent inhibition was observed, demonstrating that phosphatidylinositol-HDL can be applied to evaluation of EL inhibitor (FIG. 5).

Example 3

Measurement of Endogenous EL Activity in Plasma of EL-Transgenic Mice

Figure 6:
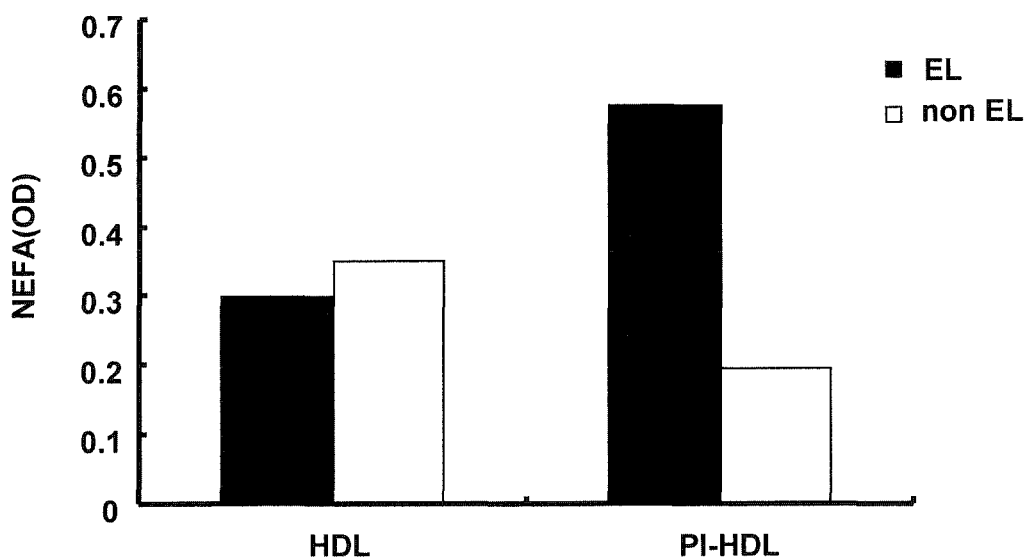
FIG. 6 shows EL activity and lipase activity other than EL (hereinafter, referred to non-EL activity) in postheparin plasma of EL transgenic mice when PI-HDL or HDL is used as a substrate. The horizontal axis and the vertical axis indicate the substrate used and the amount of NEFA, respectively.
Figure 7:
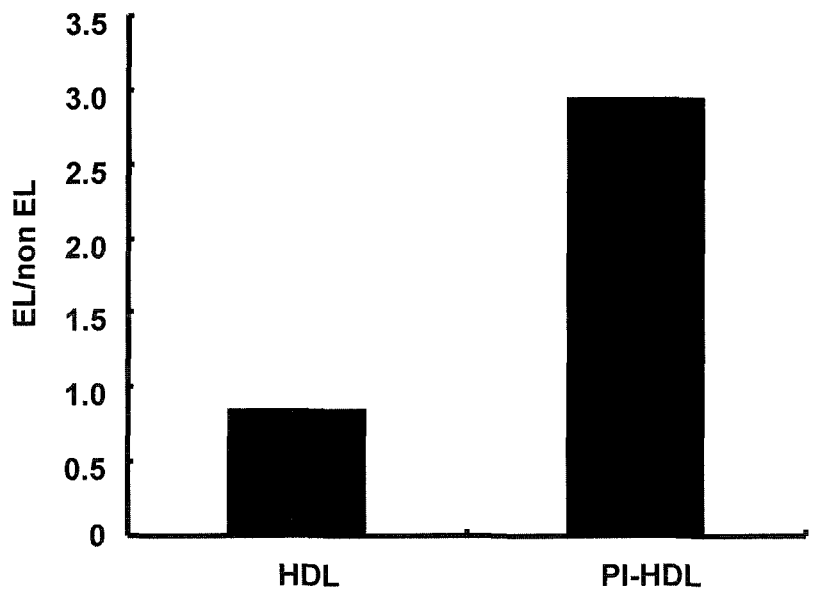
FIG. 7 shows the result converted the data shown in FIG. 6 into the ratio of EL activity to non-EL activity for PI-HDL or HDL, respectively The horizontal axis and the vertical axis indicate the substrate used and the ratio of EL activity to non-EL activity, respectively.

Phosphatidylinositol (Avanti Polar Lipids Inc.) in chloroform was collected the necessary amount, which was completely evaporated the solvent to dryness under nitrogen. After addition of PBS, phosphatidylinositol-HDL induced phosphatidylinositol (2.5 mg/ml) into HDL (5 mg/ml) was prepared by mixing phosphatidylinositol vesicle prepared by sonication on ice with human HDL (Athens Research & Technology, Inc.) and incubating at 4° C. for 24 hr. The saline (Otsuka pharmaceutical Co., Ltd.) contained 50 KU/Kg heparin (Sigma Aldrich, Co.) was injected into tail vein of EL-transgenic mice. After 30 min, the blood obtained by drawing from the abdominal vena cava was centrifuged and plasma containing endogenous EL by collecting the supernatant was obtained. Phosphatidylinositol-HDL or HDL was added to reaction solution including 100 mM Tris-HCl buffer, 5 mM calcium chloride and 150 mM sodium chloride to achieve a final concentration of 1.5 mg/ml, and finally, plasma which was treated with an excessive amount of anti-mouse EL neutralizing antibody or normal antibody was added (total volume of 10 µl). After reaction at 37° C. for 60 min, the concentration of NEFA produced by enzyme reaction was measured with NEFA C-test Wako (Wako Pure Chemical Industries, Ltd.) and the amount of NEFA (absorbance) was assumed an index of enzyme activity. The enzyme activity was calculated by subtracting the background value equivalent to the amount of endogenous NEFA in blood from the measured value in enzyme reaction (FIG. 6). The enzyme activity with anti-mouse EL neutralizing antibody was defined as non-EL activity. The EL activity was obtained by subtracting the enzyme activity with anti-mouse EL neutralizing antibody from the enzyme activity with normal antibody. As a result, the EL activity in plasma showed more apparent activity for phosphatidylinositol-HDL than HDL and it was revealed that the relative ratio of EL activity to non-EL activity (EL activity/non-EL activity) using phosphatidylinositol-HDL as a substrate was 3.5-fold higher than that using HDL as a substrate (FIG. 6, 7).

Example 4

Figure 8:
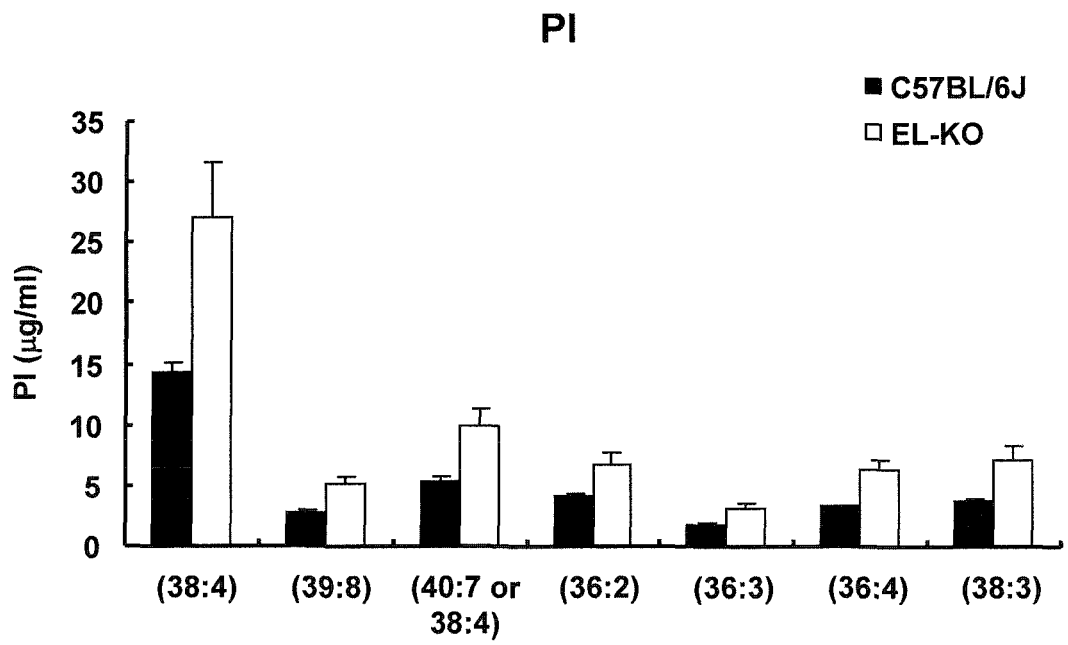
FIG. 8 shows phosphatidylinositol levels in preheparin plasma of wild-type mice (C57BL/6J strain) and EL-KO mice. The horizontal axis and the vertical axis indicate molecular species of phosphatidylinositol and phosphatidylinositol levels, respectively.
Figure 9:
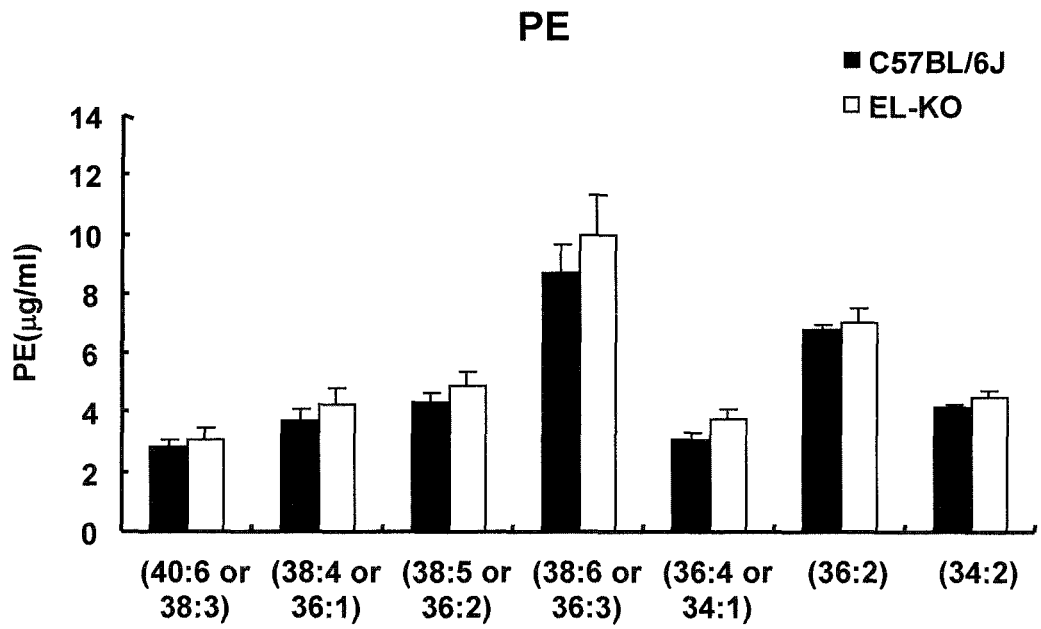
FIG. 9 shows phosphatidylethanolamine levels in preheparin plasma of wild-type mice and EL-KO mice. The horizontal axis and the vertical axis indicate molecular species of phosphatidylethanolamine and phosphatidylethanolamine levels, respectively.

Comparison of Phosphatidylinositol and Phosphatidylethanolamine Levels in Plasma Between Wild-Type Mice and EL Knockout Mice Phosphatidylinositol and phosphatidylethanolamine levels in preheparin plasma collected from C57BL/6J strain, wild-type mice and EL knockout mice were quantified by mass spectrometry with reference to Analytical Letters 2006, vol. 39, p. 957-972 (FIGS. 8 and 9). As a result, phosphatidylinositol levels in plasma of EL knockout mice showed 1.8-fold higher than that of wild-type mice, whereas phosphatidylethanolamine levels of EL knockout mice were only 1.1-fold higher than that of wild-type mice. These results demonstrated that phosphatidylinositol levels express endogenous EL activity highly sensitively.

Example 5

Figure 10:
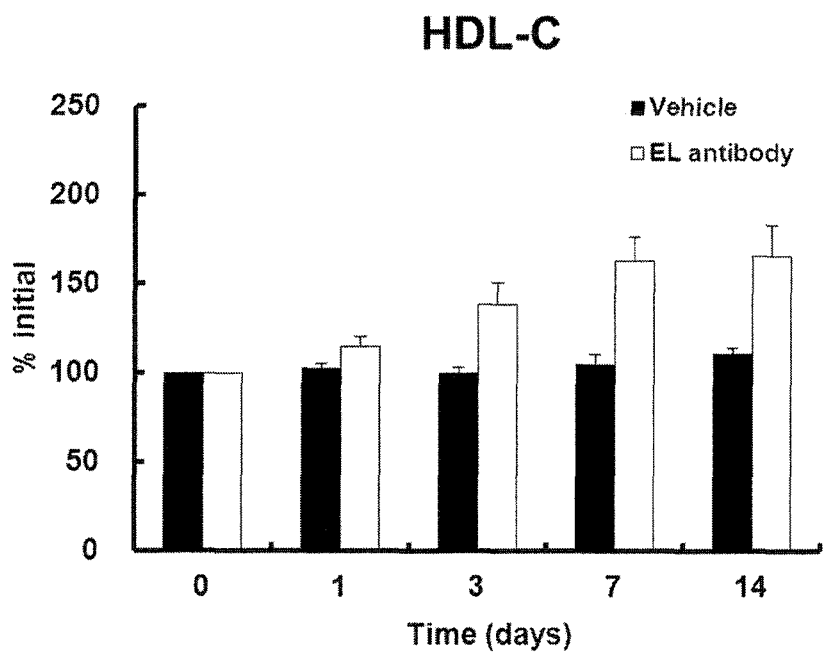
FIG. 10 shows the ratio of HDL cholesterol levels in preheparin plasma collected with time after intravenous injection of anti-EL neutralizing antibody to cynomolgus monkey to those before administration. The horizontal axis and the vertical axis indicate the sampling time of preheparin plasma after administration of anti-EL antibody and the ratio to the concentration before administration of anti-EL neutralizing antibody.
Figure 11:
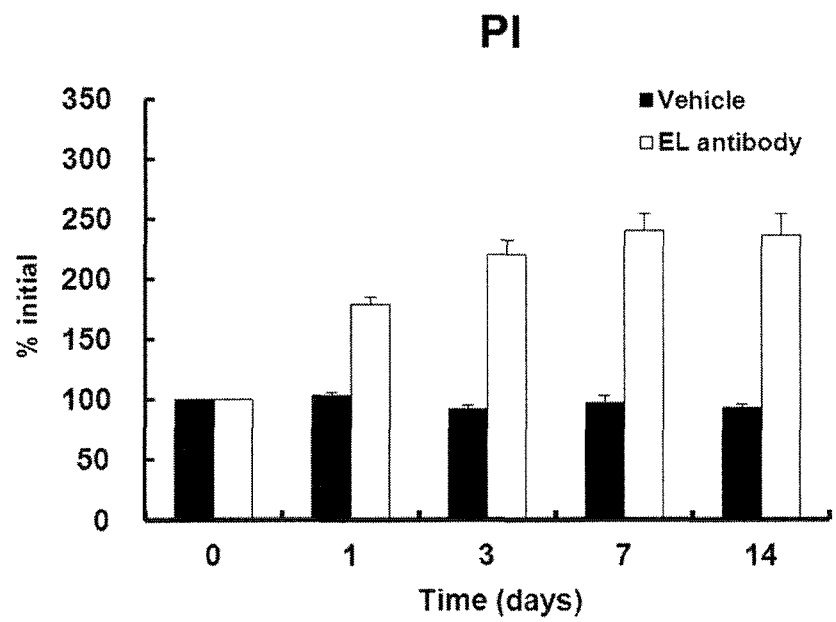
FIG. 11 shows the ratio of phosphatidylinositol levels in preheparin plasma collected with time after intravenous injection of anti-EL neutralizing antibody to cynomolgus monkey to those before administration. The horizontal axis and the vertical axis indicate the sampling time of preheparin plasma after administration of anti-EL antibody and the ratio to the concentration before administration of anti-EL neutralizing antibody.
Figure 12:
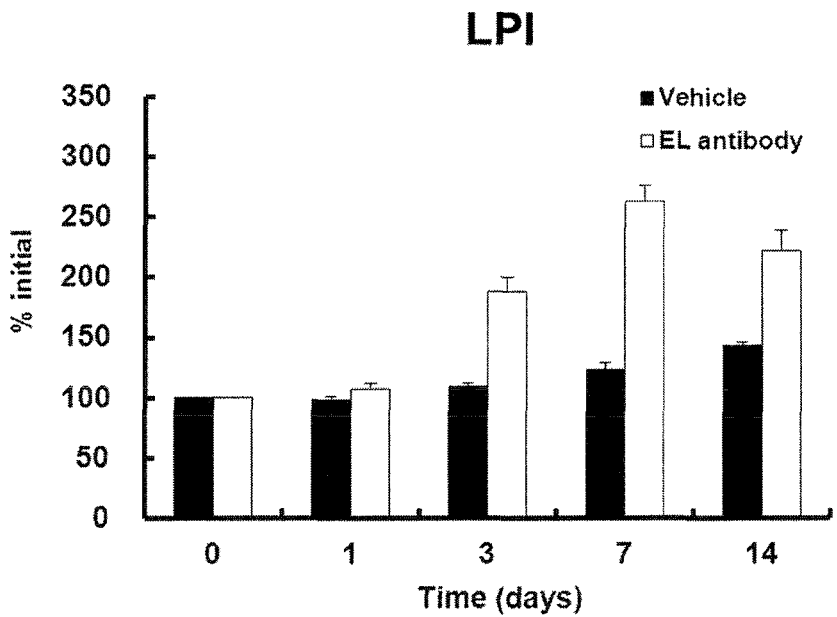
FIG. 12 shows the ratio of lysophosphatidylinositol (hereinafter, also called LPI) levels in preheparin plasma collected with time after intravenous injection of anti-EL neutralizing antibody to cynomolgus monkey to those before administration. The horizontal axis and the vertical axis indicate the sampling time of preheparin plasma after administration of anti-EL antibody and the ratio to the concentration before administration of anti-EL neutralizing antibody.

Change in HDL Cholesterol, Phosphatidylinositol and Lysophosphatidylinositol Levels in Blood after Administration of Anti-EL Neutralizing Antibody to Cynomolgus Monkey HDL cholesterol, phosphatidylinositol and lysophosphatidylinositol levels in preheparin plasma collected with time after administration of anti-EL neutralizing antibody to cynomolgus monkey were measured. HDL cholesterol was quantified by automated analyzer (FIG. 10). Phosphatidylinositol and lysophosphatidylinositol were quantified by mass spectrometry and the total amount of each molecular species was calculated (FIG. 11, 12). As a result, HDL cholesterol, phosphatidylinositol and lysophosphatidylinositol increased with time after administration of anti-EL neutralizing antibody and the increasing rate at 7 hr after administration of anti-EL neutralizing antibody showed 1.6 times in HDL cholesterol, 2.4 times in phosphatidylinositol and 2.6 times in lysophosphatidylinositol relative to each initial value before administration of antibody.

Example 6

Measurement of EL Activity Using Phosphatidylinositol-Liposomes, Phosphatidylinositol-Reconstituted HDL and Phosphatidylinositol-Detergent Mixed Micelles as a Substrate Phosphatidylinositol-liposomes are prepared appropriately with reference to The Journal Lipid Research, 1976, vol. 17 (3), p. 239-247 and-phosphatidylinositol-reconstituted HDL is prepared appropriately with reference to The Journal of Biological Chemistry, 1982, vol. 257 (8), p. 4535-4540.

On the other hand, the measurement of EL activity using phosphatidylinositol-liposomes or phosphatidylinositol-reconstituted HDL as a substrate is performed with reference to Biochemistry, 2003, vol. 42 (46), p. 13778-13785.

On the other hand, phosphatidylinositol-detergent mixed micelles are prepared appropriately with reference to The Journal of Biological Chemistry, 1988, vol. 263 (12), p. 5724-5731. Furthermore, EL activity is measured using phosphatidylinositol-detergent mixed micelles as a substrate with reference to ibid.

The invention claimed is:

1. A method for screening an inhibitor of endothelial lipase (EL) activity, comprising:
    (1) contacting phosphatidylinositol, a test substance and EL, to produce lysophosphatidylinositol,
    (2) comparing a concentration of phosphatidylinositol when the test substance is contacted with a concentration of phosphatidylinositol when the test substance is not contacted, and
    (3 selecting the test substance as an inhibitor of EL activity when the concentration of phosphatidylinositol is increased when the test substance is contacted relative to the concentration of phosphatidylinositol when the test substance is not contacted.

2. A method for screening an inhibitor of endothelial lipase (EL) activity, comprising:
    (1) contacting phosphatidylinositol, a test substance and EL, to produce lysophosphatidylinositol,
    (2) comparing a concentration of lysophosphatidylinositol when the test substance is contacted with a concentration of lysophosphatidylinositol when the test substance is not contacted, and
    (3) selecting the test substance as an inhibitor of EL activity when the concentration of lysophosphatidylinositol is decreased when the test substance is contacted relative to the concentration of lysophosphatidylinositol when the test substance is not contacted.

* * * * *